(12) United States Patent
Mao et al.

(10) Patent No.: US 7,698,926 B2
(45) Date of Patent: Apr. 20, 2010

(54) ELECTRICAL CONNECTION OF ENERGY HARVESTING DEVICES

(75) Inventors: Xinhui Mao, Shanghai (CN); HuaBin Fang, Shanghai (CN)

(73) Assignee: Honeywell International Inc., Morristown, NJ (US)

( * ) Notice: Subject to any disclaimer, the term of this patent is extended or adjusted under 35 U.S.C. 154(b) by 286 days.

(21) Appl. No.: 11/796,677

(22) Filed: Apr. 26, 2007

(65) Prior Publication Data
US 2008/0264144 A1 Oct. 30, 2008

(51) Int. Cl.
*G01N 27/00* (2006.01)
*H01L 41/00* (2006.01)

(52) U.S. Cl. .......................... 73/1.82; 73/584; 310/322; 310/323.06

(58) Field of Classification Search .................. 73/649, 73/582, 588, 659, 382 R, 1.82, 584; 310/322, 310/323.06, 324, 328–332, 311
See application file for complete search history.

(56) References Cited

U.S. PATENT DOCUMENTS

| | | | | |
|---|---|---|---|---|
| 3,583,225 A | * | 6/1971 | Wing et al. | 73/382 R |
| 3,857,279 A | * | 12/1974 | Salzer et al. | 73/582 |
| 4,412,148 A | * | 10/1983 | Klicker et al. | 310/358 |
| 4,818,313 A | * | 4/1989 | Sundberg | 156/64 |
| 4,854,494 A | * | 8/1989 | von Raben | 228/102 |
| 6,894,460 B2 | | 5/2005 | Clingman | 320/166 |
| 6,984,902 B1 | * | 1/2006 | Huang et al. | 310/26 |
| 7,116,036 B2 | * | 10/2006 | Balasubramaniam et al. | 310/322 |
| 7,173,343 B2 | | 2/2007 | Kugel | 290/1 R |
| 2005/0253571 A1 | * | 11/2005 | Frank et al. | 324/76.11 |
| 2009/0218824 A1 | * | 9/2009 | Freeland et al. | 290/1 R |

OTHER PUBLICATIONS

Piezoelectric Energy Harvesting Device Optimization by Synchronous Electric Charge Extraction; E. Lefeuvre, A. Badel, C. Richard, D. Guyomar; Journal of Intelligent Mterial Systems and Structures, vol. 16, No. 10, 865-876 (2005); Sage Journals Online.
Fabrication and Performance of a Flat Piezoelectric Cantilever Obtained Using a Sol-Gel Derived PZT Thick Film Deposited on a SOI Wafter; T. Kobayashi, et al. 2006 Smart Mater. Struct. 15.

(Continued)

*Primary Examiner*—J M Saint Surin
(74) *Attorney, Agent, or Firm*—Kris T. Fredrick; Kermit D. Lopez; Luis M. Ortiz (57) ABSTRACT

An energy harvesting system and method. An array of cantilevers with PZT films is electrically connected to an energy harvesting device that converts vibration energy to electrical energy. An AC output signal provided by the cantilevers can be rectified to a DC output, thereby avoiding impairment in total electrical output. The DC output terminals can be connected in parallel and/or in series in order to achieve a higher voltage and/or a higher current that prevents the output from different cantilevers from counteracting one another. The connection circuitry includes one or more rectifying components integrated with one or more micro-cantilevers into a single integrated circuit chip. An oscillograph can be utilized to monitor the DC output voltage signal from an associated testing circuit.

21 Claims, 12 Drawing Sheets

OTHER PUBLICATIONS

Wireless Sensor Network Node With Asynchronous Architecture and Vibration Harvesting Micro Power Generator; Y. Ammar, A. Buhrig, M. Marzencki, B. Chariot, S. Basrour, K. Matou, M. Renaudin; TIMA Laboratory, 46, av. Felix Viallet 38031 Grenoble, France.

Micro Power Sources for Autonomous Wireless Microsystems; Y. Ammar, S. Basrour, B. Charlot, M. Marzencki; Tima Mico and Nano Systems Group; TIMA Laboratory—MNS Group 2005.

* cited by examiner

ELECTRICAL CONNECTION OF ENERGY HARVESTING DEVICES

TECHNICAL FIELD

Embodiments are generally related to electrical power harvesting systems and methods. Embodiments are also related to piezoelectric energy harvesting devices. Embodiments are additionally related to connection circuitry for energy harvesting.

BACKGROUND OF THE INVENTION

Power conservation is an important factor in many electrical systems, such as but not limited to, wireless sensor networks (WSNs) that operate according to low power requirements and low data rates. Long battery life (e.g., up to 10 years) is essential in such systems where line power is not available or if the system is mobile in nature. In many applications, however, utilizing and replacing batteries, even long-lived battery types, is impractical due to factors such as, but not limited to, hard-to-access locations, and labor and replacement battery costs. Accordingly, solutions have been sought for harvesting or extracting electrical power from the environment.

Energy harvesting devices can be utilized to collect and convert environmental energy into electric energy for supporting electrical components, devices and/or systems, thereby eliminating the need for batteries. One example of an energy harvesting device or system is a cantilever(s) with Lead-Zirconate-Titanate (PZT) film(s), which can convert vibration energy in an environment into electrical energy. Piezoelectric materials can be utilized as a means for transforming ambient vibrations into electrical energy, which can be stored and used to power other devices. With the recent surge of microscale devices, piezoelectric power generation can provide convenient alternative to traditional power sources used to operate certain types of sensors/actuators, telemetry and MEMS devices. The energy produced by these materials in many cases, however, is much too small to directly power an electrical device. Therefore, the majority of research into power harvesting has focused on techniques for accumulating the energy until a sufficient amount is present, thereby allowing the intended electronics to be powered.

One single cantilever can only function in a single frequency and produces a very limited power output. The cantilevers must be connected to a cantilever array to overcome these problems. When the cantilevers are electrically connected directly, however, the AC electrical power from different cantilevers can be counteracted as they have different phases. The connection method thus cannot achieve ideal results.

Figure 1A:
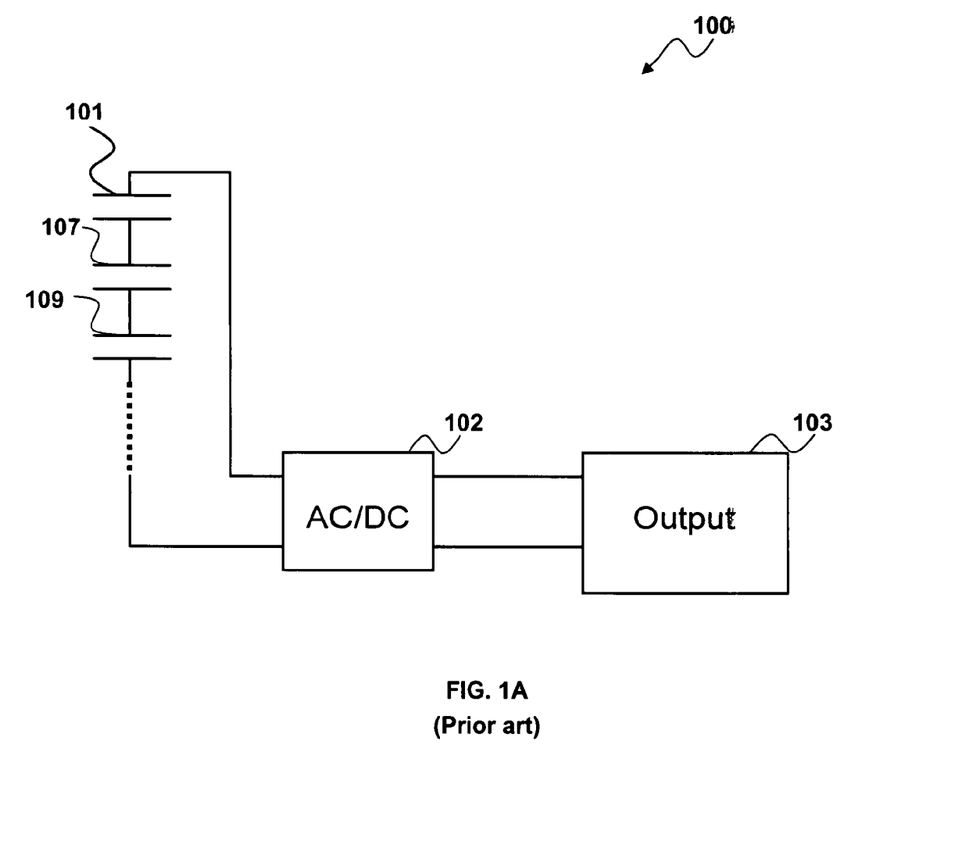
FIG. 1A illustrates a prior art representation of a connection method used in the electrical connection circuitry of an energy harvesting system, which can be implemented in accordance with an alternative embodiment.

A prior art representation of a connection configuration currently used in electrical connection circuitry of an energy harvesting system 100 is illustrated in FIG. 1A. The block diagram depicted in FIG. 1A shows a capacitor 101 connected in series with one or more other capacitors 107, 109 and so forth. A signal can be provided to an AC/DC converter 102 to attain a high voltage output 103. In the prior art configuration depicted in FIG. 1A, the output from different cantilevers counteract.

Figure 1B:
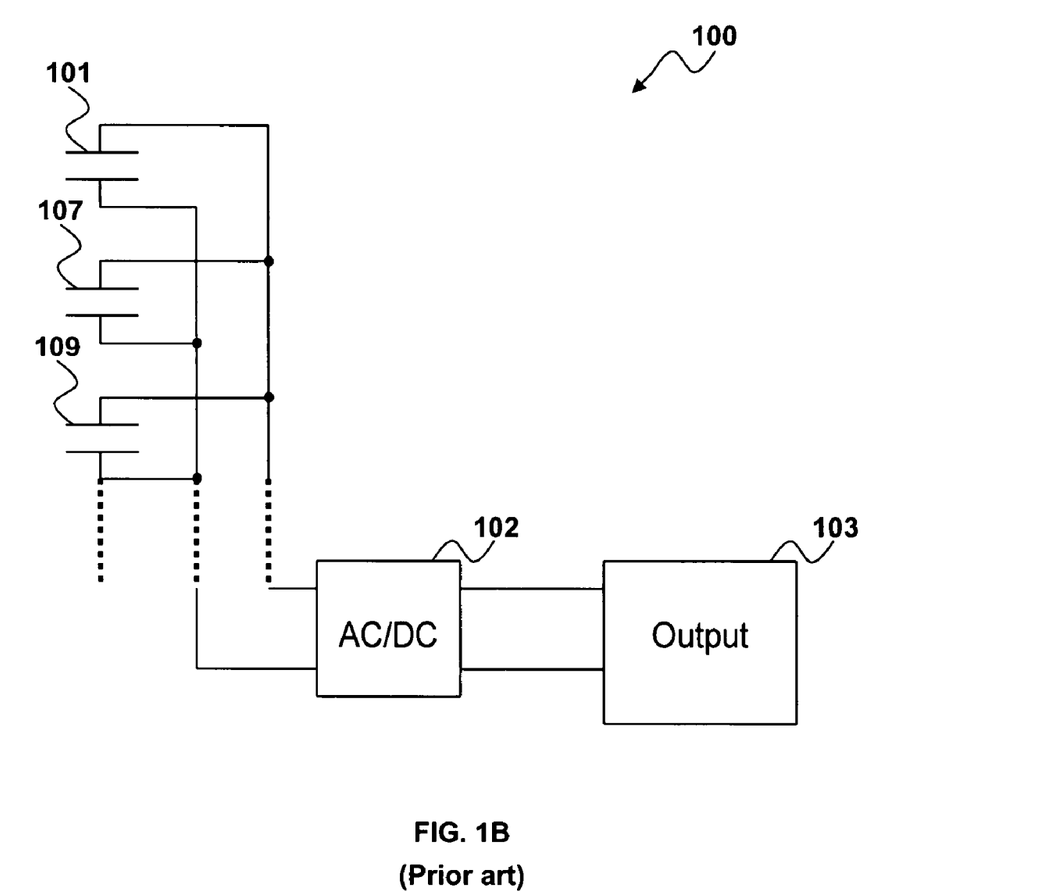
FIG. 1B illustrates another prior art representation of a connection method used in the electrical connection circuitry of an energy harvesting system, which can be implemented in accordance with an alternative embodiment.

Another prior art connection configuration currently utilized in the electrical connection circuitry of an energy harvesting system 100 is illustrated in FIG. 1B. Note that in FIGS. 1A-1B, similar or identical parts are generally indicated by identical reference numerals. Thus, a block diagram depicted in FIG. 1B illustrates capacitor 101 connected in parallel with capacitors 107, 109 and so forth. A signal can be provided to the AC/DC converter 102 to attain a high voltage output 103. In the configuration of system 100 depicted in FIG. 1B, the output from different cantilevers can also counteract.

Based on the foregoing, it is believed that a need exists for an energy harvesting device that overcomes such problems. It is believed that the system and method disclosed herein provides a solution to these problems by offering a configuration in which a DC output can be attained by rectifying an AC output from a cantilever array and DC output terminals are connected in parallel or in series to achieve a higher voltage or current output such that the output from different cantilevers cannot be counteracted.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved system and method for electrical power harvesting.

It is another aspect of the present invention to provide for an improved energy harvesting device incorporating a piezoelectric material.

It is a further aspect of the present invention to provide for connection circuitry for integrating rectifying components and micro-cantilevers into a single IC (Integrated Circuit) chip.

The aforementioned aspects and other objectives and advantages can now be achieved as described herein. An energy harvesting method and system is disclosed, which includes the use of a waveform generator for generating a signal, and a vibrator for providing mechanical vibrations in order to characterize the performance of an Energy Harvesting (EH) device. The vibrator can be program-controlled by the waveform generator. An accelerator can also be attached to the vibrator, wherein the accelerator measures the vibration strength of mechanical vibrations and an amplitude or velocity of the signal, thereby permitting a clamped component subject to the accelerator and the vibrator to provide converted vibration energy in the form of an AC signal that is rectified to a DC voltage output in order to achieve an electrical energy in the form of a higher voltage or a current output that is harvested and utilized to characterize the electrical functioning of an associated electrical system or device.

A power amplifier can also be integrated with the waveform generator to drive the vibrator and regulate vibration strength of the mechanical vibrations. Additionally, an accelerator monitor can be associated with the accelerator, wherein the accelerator monitor delivers a signal strength associated with the signal. The clamped sample or clamped component can be implemented in one embodiment as cantilever array. In another embodiment, the clamped sample may be provided as a cantilever array with nickel mass. A testing circuit can also be provided, which includes a bridge rectifier and a capacitor. The testing circuit detects the electrical energy harvested and is generally utilized to support the electrical functioning of the associated electrical system or device.

An oscillograph can also be connected to the testing circuit, wherein the oscillograph monitors a DC output voltage signal generated by the testing circuit. The bridge rectifier associated with the testing circuit generally comprises at least four diodes connected electrically in series with one another. A laser displacement sensor can also be provided for tip displacement testing, wherein the laser displacement sensor is connected to the clamped component. Such a laser displacement sensor can include a laser source and a signal controller in association with the laser source. The laser displacement sensor further includes an optical tuner setup module associated with the laser source and the signal controller; and a data-processing apparatus for data storage and processing. Such a data-processing apparatus is associated with the laser source, the signal controller and the optical tuner setup module.

The use of a cantilever array (i.e., clamped component) can overcome issues of frequency and power output encountered with the case of a single cantilever. When the cantilevers are electrically connected directly, the AC electrical power from different cantilever can be counteracted due to their different phases. Instead of electrically connecting the cantilevers of an energy harvesting device directly, the AC output can be rectified to a DC output. The DC output terminals can be connected in parallel or in series to achieve a higher voltage or output current. The connection circuitry, including the rectifying components, can be integrated with one or more micro cantilevers into a single IC chip.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 2:
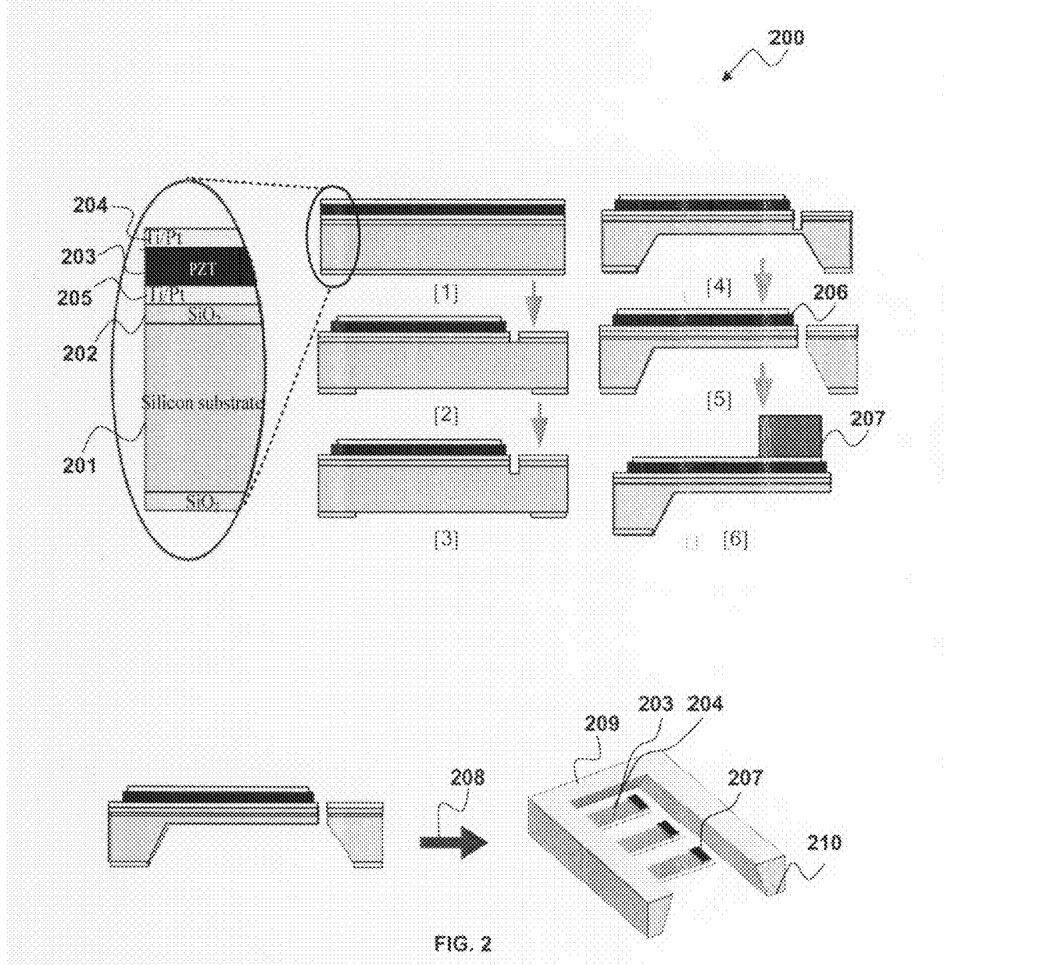
FIG. 2 illustrates a process flow diagram depicting a method for fabricating a cantilever, in accordance with a preferred embodiment.

FIG. 2 illustrates a process flow diagram depicting a method 200 for fabricating a cantilever, in accordance with a preferred embodiment. A general flow process is depicted in FIG. 2 with respect to illustrative steps [1], [2], [3], [4], [5], and [6]. As indicated at step [1], a (100) oriented silicon substrate 201 of 500 μm thickness, can be wet-oxidized. Note that the value of 500 μm is merely an illustrative and suggested value only and is not considered a limiting feature of the embodiments. The same is also true for other parameters and values discussed herein. A layer of 2 μm thick silicon oxide 202 serves to improve the adhesion of a functional layer to the silicon substrate 201 surface and can act as a mask during a later-implemented wet etching operation.

Thereafter, a Pt/Ti bottom electrode 205, (e.g., of 30 nm thick Ti and (111) oriented 300 nm thick Pt successively) can be sputtered on the layer of silicon oxide 202. Next, one or more lead-zirconate-titanate (PZT) films 203 can be deposited according to a sol-gel operations to achieve a crackless PZT film 203 layer. One or more, Ti/Pt top electrodes 204 can then be sputtered upon the PZT film layer 203. Thereafter, as indicated at step [2], the silicon substrate 201 with the prepared PZT film layer 203 can be patterned utilizing a standard photolithography technique.

As indicated at step [3], a black-oxide window with alignmarks can be created through the use of HF solution etching and front electrodes and the PZT film layer 203 can then be patterned in an orderly manner, by employing reactive ion etching (RIE) and wet etching respectively, through a double-side alignment process. Next, KOH chemical etching can be utilized for bulk silicon substrate 201 micromachining as indicated at step [4]. In order to prevent the KOH solution from eroding the PZT film layer 203, a delicate jig can be employed to protect the PZT film layer 203 and the wet etching process can be halted. Thereafter, as depicted at step [5], a silicon RIE processing operation can then be utilized to release the formed composite cantilever 206.

Next, as indicated at step [6], a well-chosen nickel mass 207 can be fabricated utilizing, for example, an UV-LIGA SU-8 technique and affixed to the composite cantilever 206 utilizing a glue. Following completion of the wire bonding process, the PZT film layer 203 can be poled by applying, for example, a 160 V/cm DC voltage for five minutes. The resulting cantilevers 206 composed of, for example, Pt/Ti/PZT/Pt/Ti/SiO2/Si/SiO2 multilayered structures, are found to be flat. An arrow 208 indicates a section of cantilever 206 depicted in FIG. 2 illustrating a dielectric 209, a Pt/Ti top electrode 204, the PZT film layer 203, nickel mass 207 and a silicon base 210.

Figure 3:
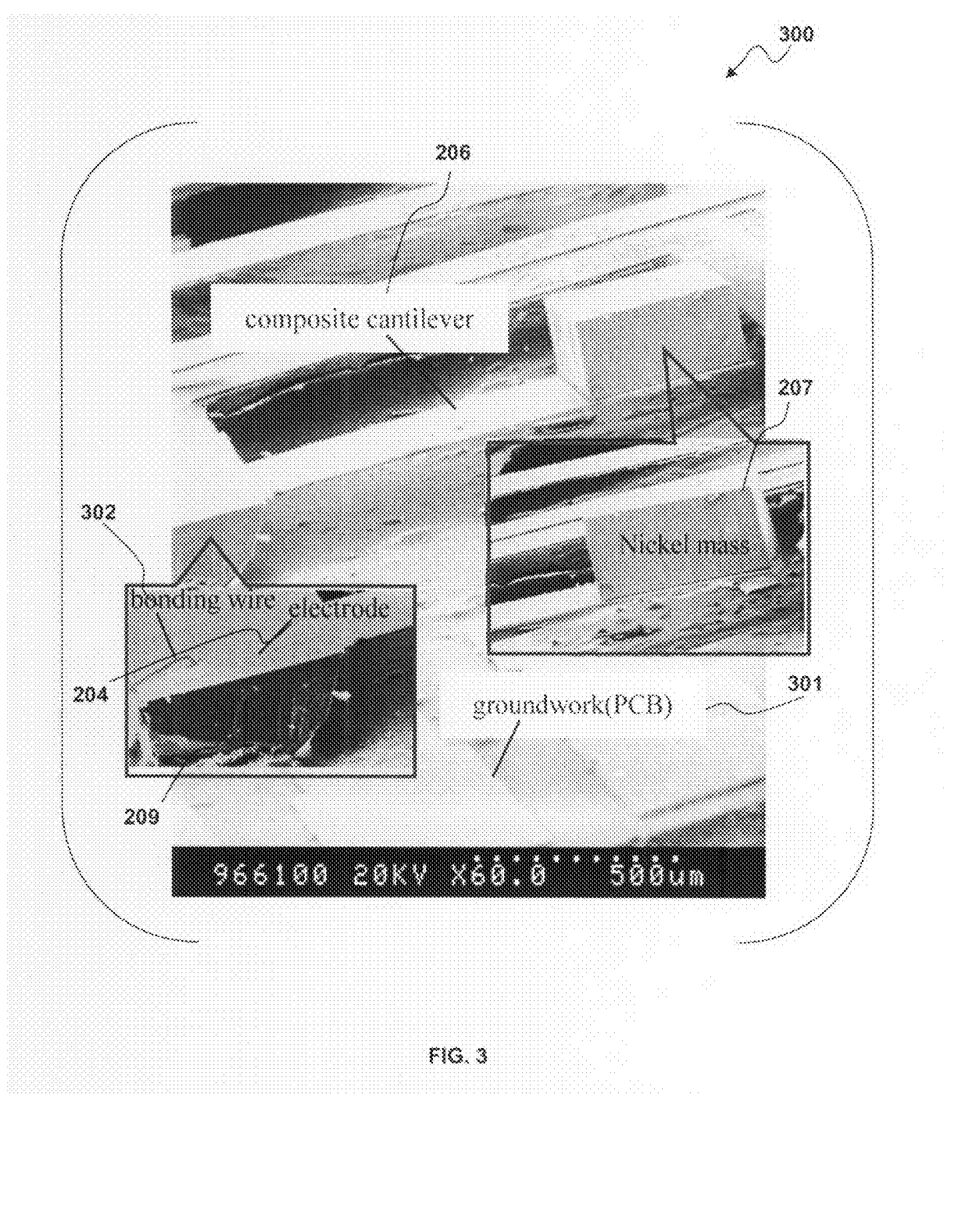
FIG. 3 illustrates a pictorial view of a SEM of a cantilever micromachined on a PCB (Printed Circuit Board), in accordance with an alternative embodiment.

FIG. 3 illustrates a pictorial view of a screen shot of a view provided an SEM (Scanning Electron Microscope) of a configuration 300 that includes a cantilever 206 micromachined on a PCB 301, in accordance with an alternative embodiment. Note that an SEM is a type of electron microscope capable of producing high-resolution images of a sample surface. Due to the manner in which the image is created, SEM images have a characteristic three-dimensional appearance and are useful for judging the surface structure of the sample. Note that in FIGS. 2-8 herein, identical or similar parts or elements are generally indicated by identical reference numerals. As indicated in FIG. 3, the composite cantilever 206 can be mounted on the PCB 301. The cantilever 106 generally contains a nickel mass 207 and a silicon base 210. The cantilever 206 additionally includes one or more shortened Pt/Ti top electrodes 204 and the PZT film layer 203 discussed earlier. A bonding wire 302 generally ties the cantilever 206 to the PCB 301.

Figure 4:
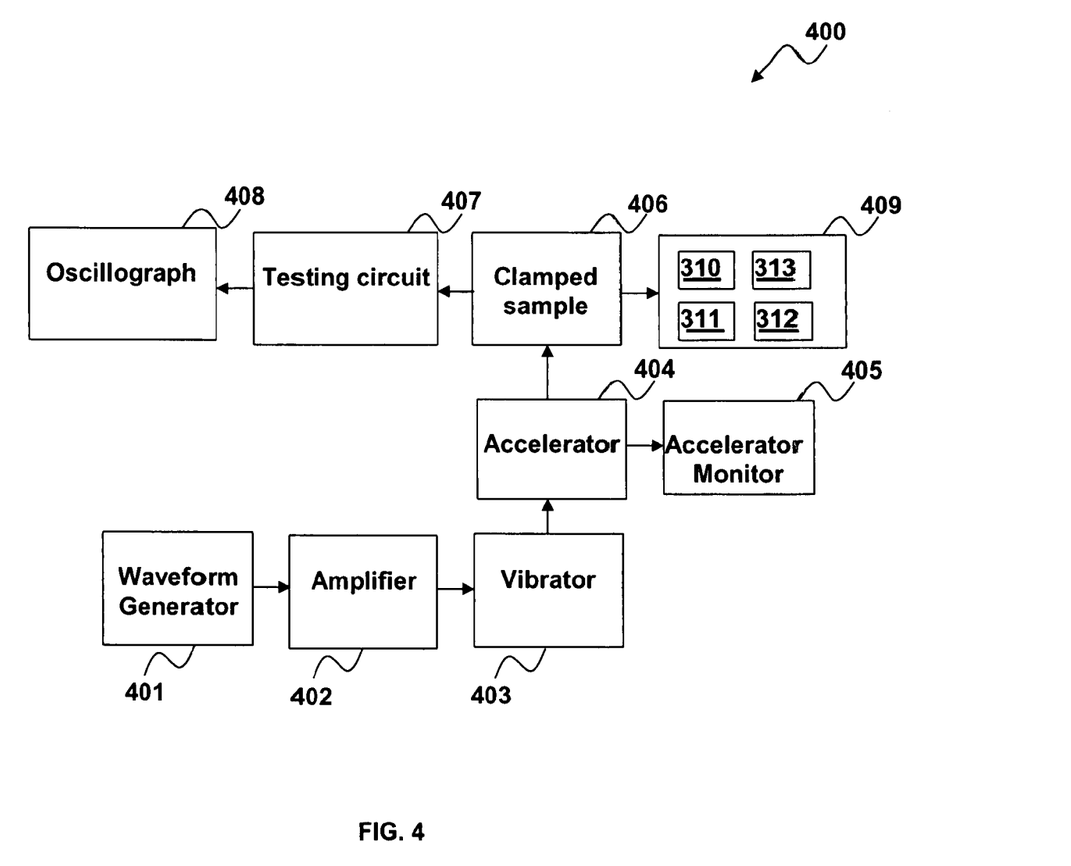
FIG. 4 illustrates a block diagram of an electrical energy harvesting system, which can be implemented in accordance with a preferred embodiment.

FIG. 4 illustrates a block diagram of an electrical energy harvesting system 400, which can be implemented in accordance with a preferred embodiment. The electrical energy harvesting system 400 generally includes a vibrator 403, which can be utilized to supply reliable mechanical vibrations to a clamped sample 406. The vibrations can be program controlled by an arbitrary waveform generator 401. Additionally, the electrical energy harvesting system 400 includes a power amplifier 402 that can be incorporated into and associated with the waveform generator 401 to drive the vibrator 403 and regulate vibration strength. The electrical energy harvesting system 400 further includes an accelerator 404 that can be attached to the spindle of the vibrator 403, such that a resulting vibration strength, an acceleration, an amplitude and/or a velocity can be measured and a signal strength thereof delivered to an accelerator monitor 405.

The electrical energy harvesting system 400 further includes an oscillograph 408 that can be utilized to monitor one or more voltage signals from the clamped sample 406. For power generation, a testing circuit 407 can also be employed by system 400, which includes a bridge rectifier 601 circuit and an electrical storage capacitor 602 utilized for harvesting the electrical energy. A common four-germanium-diodes bridge rectifier 601 circuit, with a diode forward bias voltage of, for example, 0.18V at steady state, can be introduced for rectification purposes. A varying resistor (not shown in figure) connected to the power generator 501 can be monitored utilizing the oscillograph 408 in order to measure and calculate the power output. The system 400 can also include the use of a laser displacement sensor 409, which can be introduced for tip displacement testing. The laser displacement sensor 409 includes a laser source 310, a signal controller 311, an optical tunable setup module 312, and a data-processing apparatus or computer 313 for data storage and processing.

Figure 5:
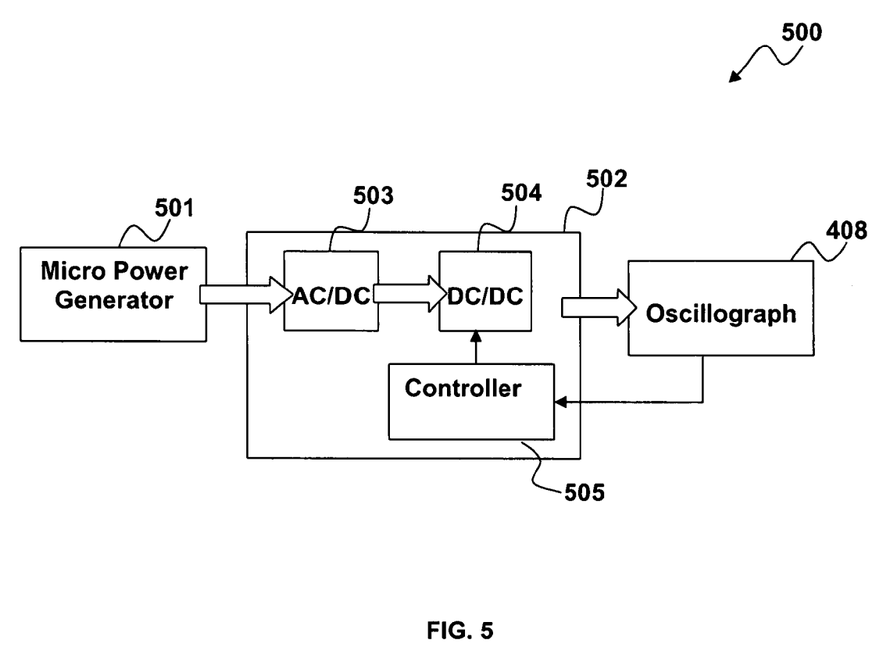
FIG. 5 illustrates a block diagram indicating the architecture of a power management module, which can be implemented in accordance with an alternative embodiment.

FIG. 5 illustrates a block diagram depicting the architecture of a power management module 500, in accordance with an alternative embodiment. Again, as a reminder, in FIGS. 2-8 discussed and illustrated herein, identical or similar parts or elements are generally indicated by identical reference numerals. The power management module 500 includes a micro-power generator 501 that is composed of a nickel mass 207 connected to the silicon substrate 201 by the flexure cantilever 206 discussed earlier. When the structure composed of the cantilever 206 and the nickel mass 207 is excited by vibrations, the structure can oscillate within its respective frequency mode shapes. During the movement, the cantilever 206 can be stressed in compression and elongation on the upper and bottom surfaces. The PZT film layer 203 placed on the top of the cantilever 206 can be stressed and by consequence, some electrical energy charges can appear on the surface of the PZT film layer 203.

These charges can be collected by metallic electrodes and transmitted to an energy harvesting circuit 502. The signal provided by the generator 501 is generally an AC (Alternating Current) signal and the voltage is typically very low. By consequence, some operations of voltage rectification and elevation are required. These operations can be configured with the best efficiency such that the circuit 502 possesses very low power consumption. The energy harvesting circuit 502 can be composed of an AC/DC circuit 503 for rectification, and a DC/DC circuit 504 for elevation of the voltage. The DC/DC circuit 504 can be managed by a digital controller 505, since it is an active circuit that can adapt depending on the incoming electrical signal to maximize the energy transfer. The output DC voltage can be measured by the oscillograph 408. Because of the phase differences of each cantilever 206, the parallel/serial connection impairs the total electrical output before rectification. After rectification, the DC electrical energy can be accumulated. Therefore, voltage increases under a serial connection and the voltage difference is split with respect to a parallel connection thereof.

Figure 6:
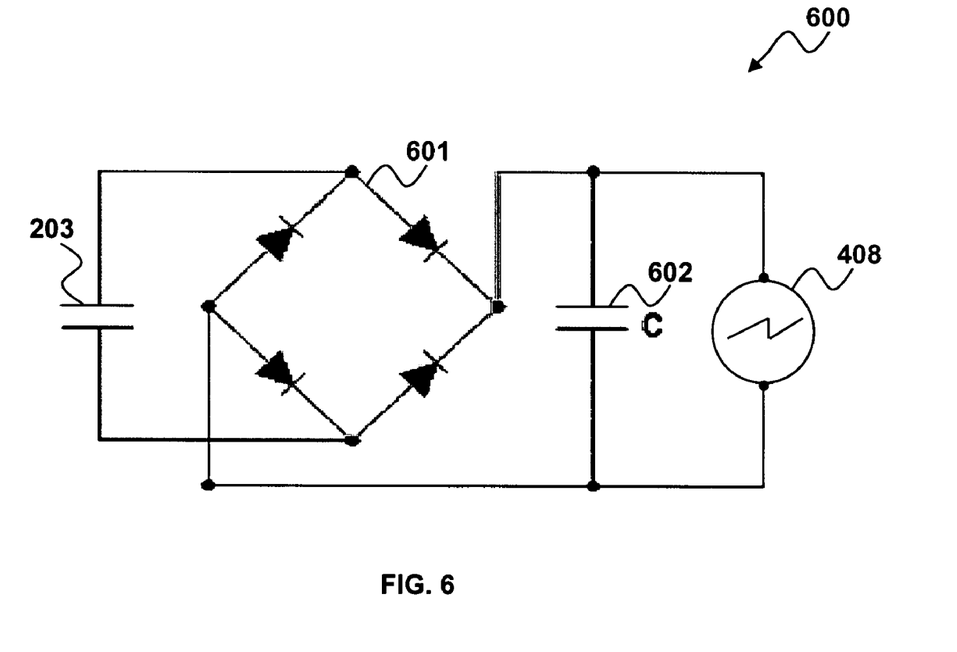
FIG. 6 illustrates a schematic view of a circuit diagram of a testing system, which can be implemented in accordance with an alternative embodiment.

FIG. 6 illustrates a circuit diagram depicting a testing circuit 600, which can be implemented in accordance with a preferred embodiment. The circuit 600 comprises a bridge rectifier 601, a capacitor 602 and an oscillograph 408 for measuring the voltage output. The voltage produced by PZT film layer 203 can be first fully wave rectified and then accumulated in a large capacitor 602 such that the DC voltage across the capacitor 602 can be thereafter measured by the oscilloscope 408 described earlier. The simplicity of circuit 600 allows circuit 600 to be constructed very compactly and without additional components, which may result in increased power dissipation.

Figure 7:
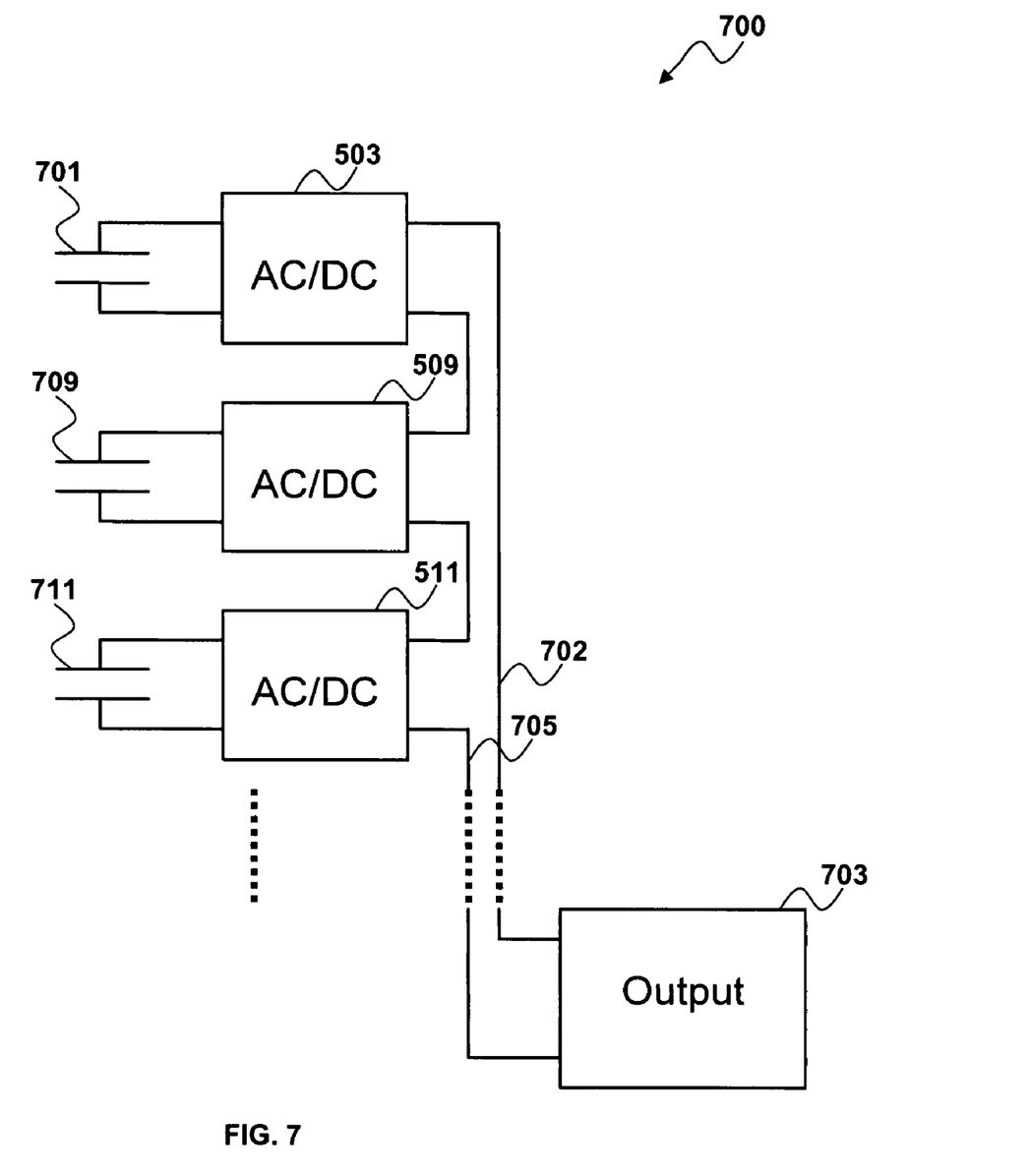
FIG. 7 illustrates a block diagram indicating the electrical connection circuitry 700 of an energy harvesting system 400 in which the DC output terminals are connected in series in accordance with a preferred embodiment.

FIG. 7 illustrates a block diagram illustrating the electrical connection circuitry 700 of the energy harvesting system 400 described earlier in accordance with a preferred embodiment. The electrical connection circuitry 700 depicted in FIG. 7 generally includes one or more DC output terminals 702 and 705, which can be respectively connected in a series configuration. The DC output terminal 702, for example, is connected to the AC/DC circuit 503 in order to provide a higher voltage output 703. The DC output terminal 705 can, for example, be output from the AC/DC circuit 511 to provide the higher voltage output 703. A capacitor 701 is generally connected to the AC/DC circuit 503. Similarly, in the configuration depicted in FIG. 7, a capacitor 709 is connected to an AC/DC circuit 509, and a capacitor 711 is connected to an AC/DC circuit 511, and so forth. The AC output can be rectified firstly to DC output by one or more of the AC/DC circuits 503, 509, 511 and so forth. The DC output terminals 702 can be connected in series to obtain the higher voltage output 703.

Figure 8:
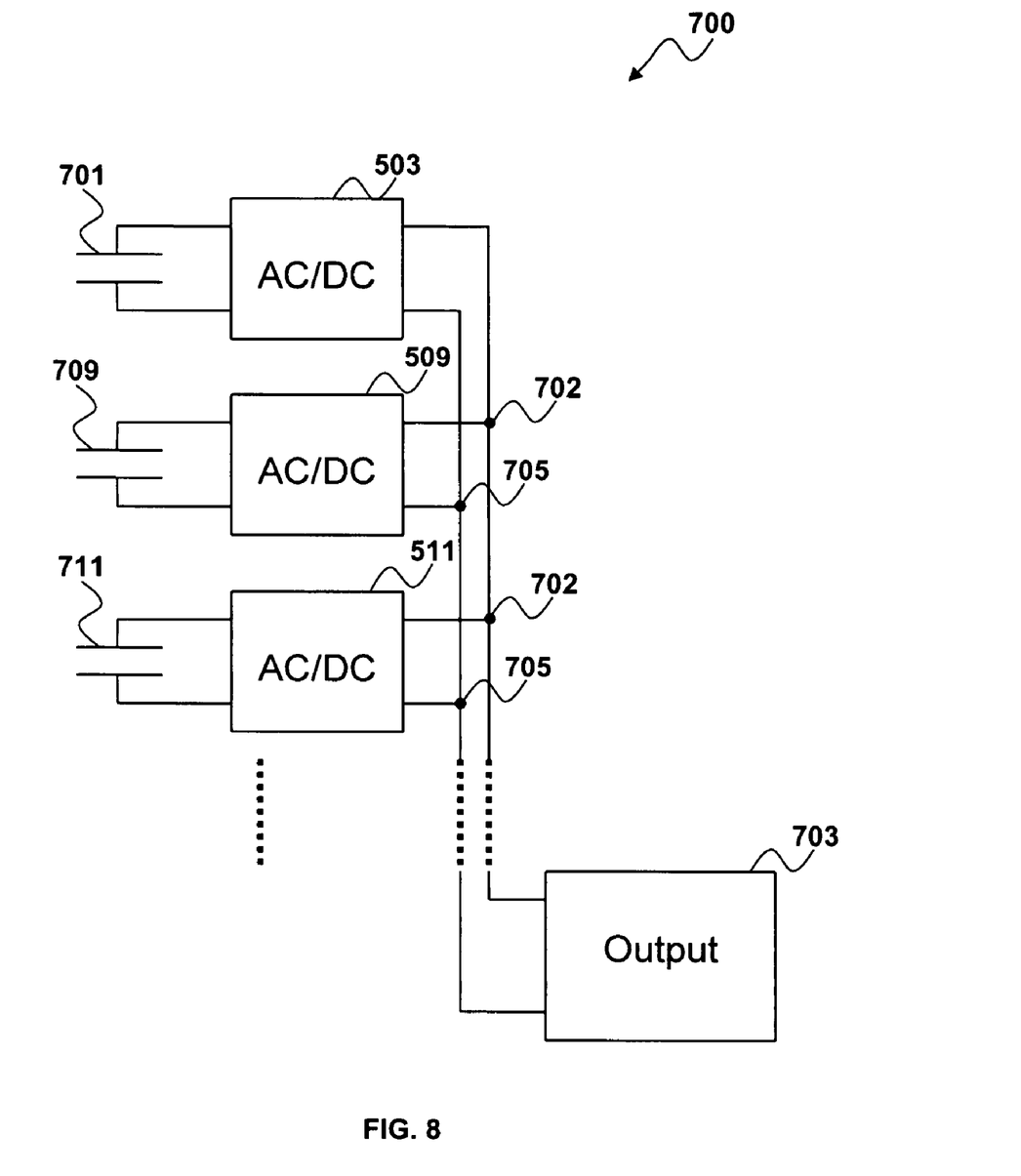
FIG. 8 illustrates a block diagram indicating the electrical connection circuitry 700 of an energy harvesting system 400 in which the DC output terminals are connected in parallel in accordance with a preferred embodiment.

FIG. 8 illustrates a block diagram indicating the electrical connection circuitry 700 of the energy harvesting system 400 in which the DC output terminals 702, 705 are connected in a parallel arrangement in accordance with an alternative embodiment. Note that in FIGS. 7-8, identical or similar parts or elements are generally indicated by identical reference numerals. The AC output can be rectified firstly to DC output by an AC/DC circuit 503. The DC output terminals 702 can be connected in parallel to obtain a higher current output 703.

Figure 9A:
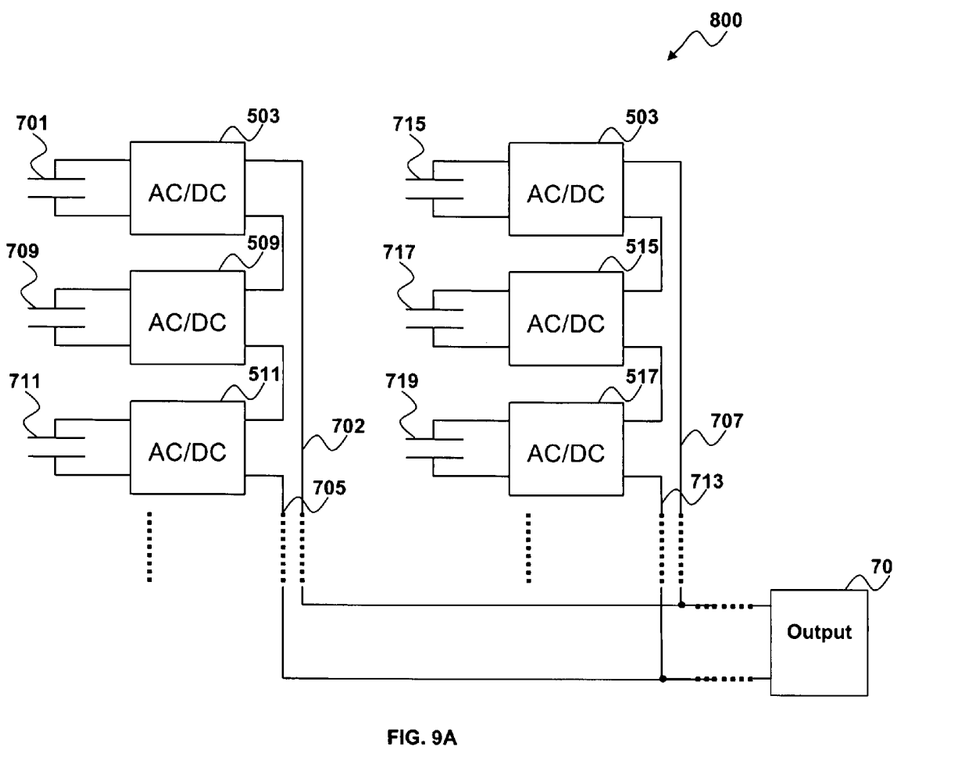
FIG. 9A illustrates a block diagram indicating the electrical connection circuitry 800 of an energy harvesting system 400 in which parallel and series connection of the DC output terminals 702, 707, 705 and 713 can be employed at the same time to improve the voltage and current output connected in parallel and in series in accordance with an alternative embodiment.

FIG. 9A illustrates a block diagram indicating the electrical connection circuitry 800 of an energy harvesting system 400 in which parallel and series connection of the DC output terminals 702, 707, 705 and 713 can be employed at the same time to improve the voltage and current output connected in parallel or in series in accordance with an alternative embodiment. The electrical connection circuitry 800 depicted in FIG. 9A generally includes one or more DC output terminals 702, and 707, which can be respectively connected in a series configuration. The DC output terminals 702 and 707, for example, are connected to the AC/DC circuits 503 and 513 in order to provide a higher voltage output 703. The DC output terminal 705 and 713 can, for example, be output from the AC/DC circuit 511 and 517 to provide the higher voltage output 703.

The capacitors 701 and 715 are generally connected to the AC/DC circuits 503 and 513. Similarly, in the configuration depicted in FIG. 9A, capacitors 709, 717 are connected to AC/DC circuits 509 and 515, and capacitors 711, 719 are connected to an AC/DC circuits 511 and 517, and so forth. The AC output can be rectified firstly to DC output by one or more of the AC/DC circuits 503, 509, 511 and so forth. The DC output terminals 702 can be connected in series to obtain the higher voltage output 703. Similarly the DC output terminals 707 can be connected in series to obtain the higher voltage 703. The DC output terminals 702, 707, 705 and 713 can be connected in parallel to obtain higher current output 703. Two methods can thus be utilized in single circuit at the same time.

Figure 9B:
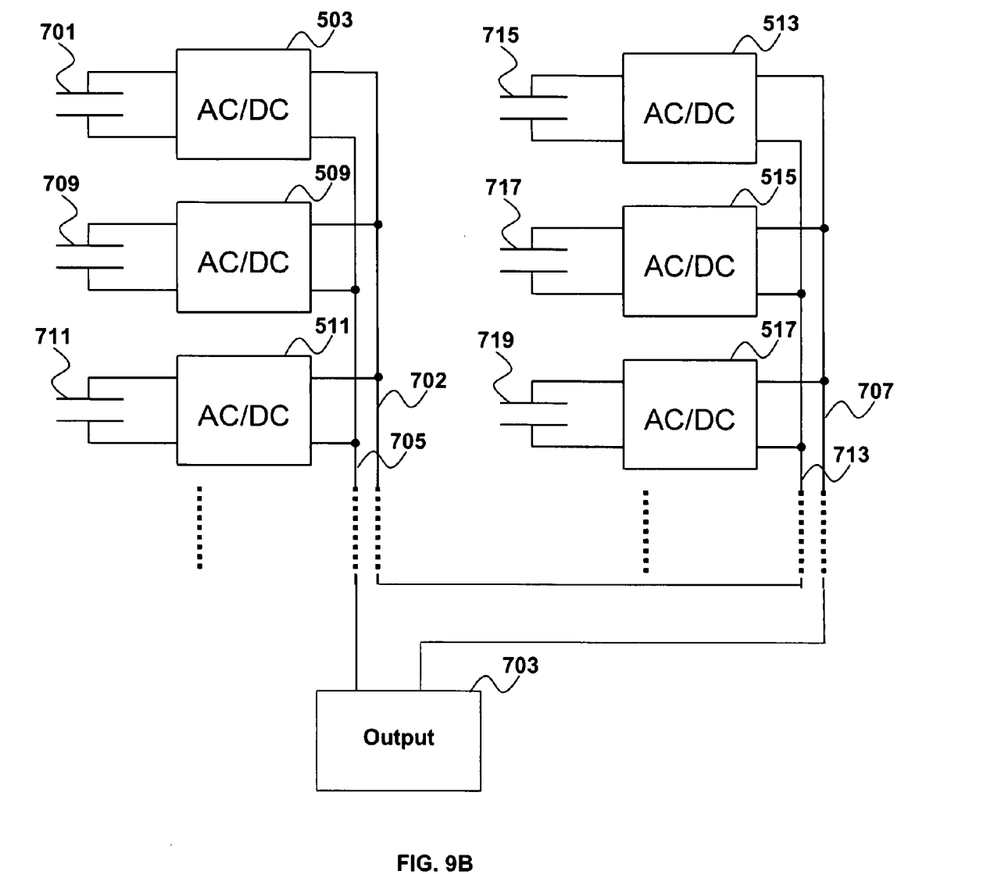
FIG. 9B illustrates a block diagram indicating the electrical connection circuitry 800 of an energy harvesting system 400 in which parallel and series connection of the DC output terminals 702 and 707 can be employed at the same time to improve the voltage and current output connected in parallel and in series in accordance with an alternative embodiment.

FIG. 9B illustrates a block diagram indicating the electrical connection circuitry 800 of an energy harvesting system 400 in which parallel and series connection of the DC output terminals 702, 705, 707 and 713 can be employed at the same time to improve the voltage and current output connected in parallel or in series in accordance with an alternative embodiment. A block diagram depicted in FIG. 9B includes a capacitor 701 connected in parallel with one or more other capacitors 709, 711 and a capacitor 715 connected in parallel with capacitors 717, 719 and so forth. The electrical connection circuitry 800 depicted in FIG. 9B generally includes one or more DC output terminals 702, 705, 707, and 713 which can be respectively connected in a parallel configuration. The AC output can be rectified to DC output by AC/DC circuits 503, 513 and so forth. The DC output terminals 702, 705, 707 and 713 can be connected in parallel to obtain a higher current output 703. The DC output terminals 702 and 707 can be connected in series to obtain a higher voltage output 703. Two methods can thus be simultaneously or alternatively utilized in a single circuit. Note that in FIGS. 7-9B, identical or similar parts or elements are generally indicated by identical reference numerals.

Figure 10:
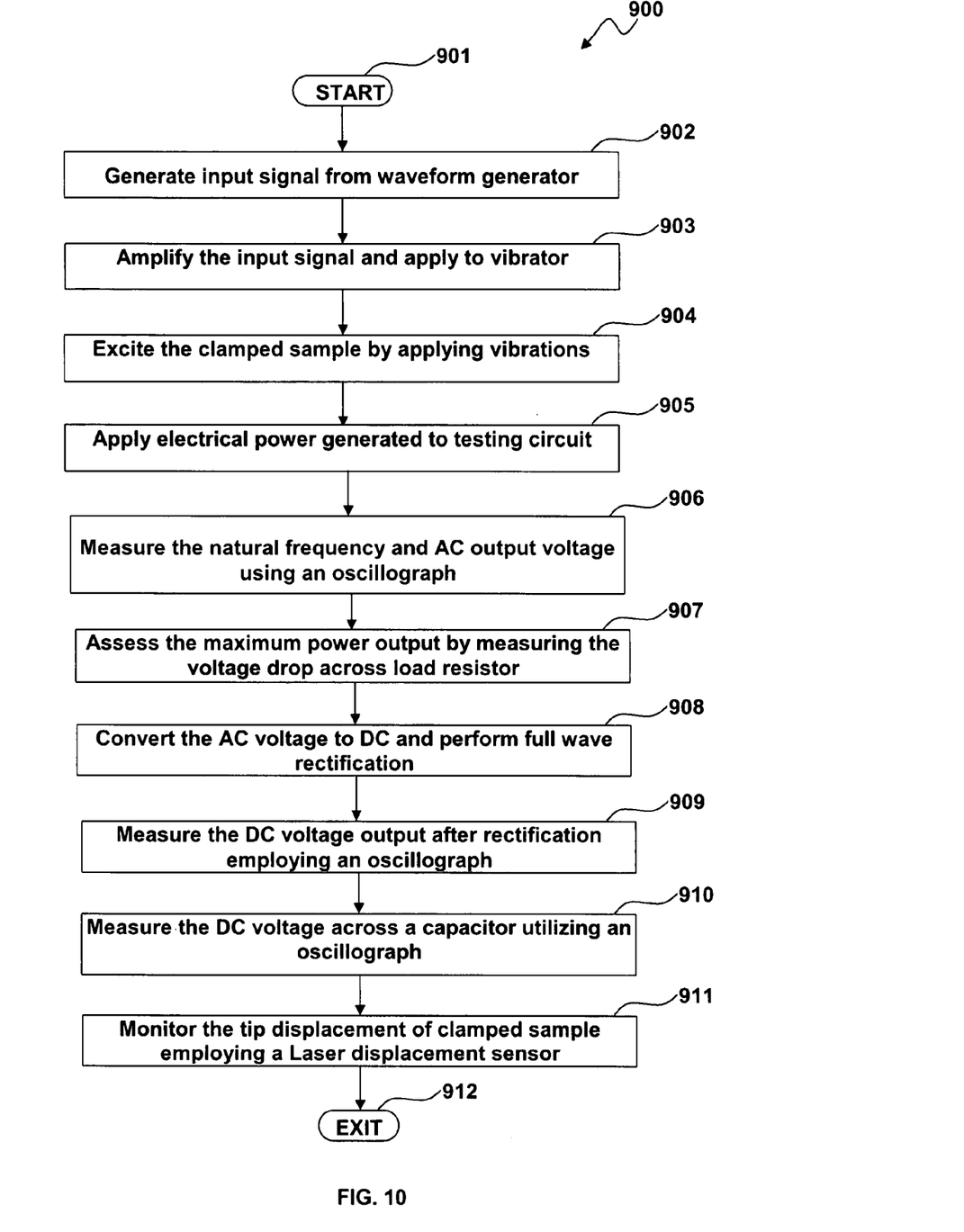
FIG. 10 illustrates a high-level flow chart of operations depicting logical operational steps of a method for electrical power harvesting, which can be implemented in accordance with a preferred embodiment.

FIG. 10 illustrates a flow chart of operations depicting logical operational steps of a method 900 for electrical power harvesting, which can be implemented in accordance with a preferred embodiment. The process begins as depicted at block 901. Thereafter, as depicted at block 902, an alternative input signal can be generated by the waveform generator 401. Next, as indicated at block 903, the input signal can be amplified and applied to the vibrator 403. As illustrated next at block 904, the clamped sample 406 can be excited by vibrations and as a result of this operation, electrical charges are generated. Thereafter, as indicated at block 905, the electrical charge generated by the piezoelectric layer in the clamped sample 906 can be employed to the testing circuit. The natural frequency and AC output voltage can then be measured by the oscillograph 408 as depicted at block 906.

Next, as depicted at block 907, maximum power output can be measured by calculating the voltage drop across a load resistor (not shown in figure). Thereafter, the AC voltage signal can be converted to DC voltage utilizing an A/D converter and a full wave rectification operation can be performed as indicated at block 908. Next, as illustrated at block 909, the DC voltage after rectification can be measured employing the oscillograph 408. The DC electricity can be accumulated and measured across a capacitor utilizing the oscillograph 408 as indicated at block 910. Next, as depicted at block 911, the tip displacement of the clamped sample 406 can be monitored by employing the laser displacement sensor 409. The process can then terminate as depicted at block 912.

The invention can be utilized in cases where AC sources have phase-difference problem and can be counteractive when connected. The method finds application with micromachined beams with PZT films and also macro PZT vibrating devices.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An electrical energy harvesting system, comprising:
    a waveform generator to generate a signal;
    a vibrator for providing mechanical vibrations, wherein said vibrator is program-controlled by said waveform generator; and
    an accelerator attached to said vibrator, wherein said accelerator measures a vibration strength of said mechanical vibrations and an amplitude or velocity of said signal, and through a partnering dynamic, contribute to allow a clamped component to provide converted vibration energy in the form of an AC signal, wherein said AC signal is utilized in a predominately non-diagnostic role and subsequently rectified to a DC voltage output in order to achieve an electrical energy in the form of a higher voltage or a higher current output that is harvested and utilized to characterize the electrical functioning of an associated electrical system or device.

2. The system of claim 1 further comprising a power amplifier integrated with said waveform generator to drive said vibrator and regulate a vibration strength of said mechanical vibrations; and an accelerator monitor associated with said accelerator, wherein said accelerator monitor delivers a signal strength associated with said signal.

3. The system of claim 1 wherein said clamped component comprises a plurality of nickel mass sections, wherein each nickel mass section is positioned on each of a cantilever array segment of a cantilever array, positioned thereon to accentuate an inertial momentum.

4. The system of claim 1 further comprising a testing circuit comprising a bridge rectifier and a capacitor, wherein said testing circuit detects said electrical energy harvested and utilized to support the electrical functioning of an associated electrical system or device.

5. The system of claim 4 further comprising an oscillograph connected to said testing circuit, wherein said oscillograph monitors a DC output voltage signal generated by said testing circuit.

6. The system of claim 4 wherein said bridge rectifier comprises at least four diodes connected electrically in series with one another.

7. The system of claim 1 further comprising a laser displacement sensor for tip displacement testing, wherein said laser displacement sensor is connected to said clamped component.

8. The system of claim 7 wherein said laser displacement sensor further comprises:
a laser source;
a signal controller in association with said laser source;
an optical tuner setup module associated with said laser source and said signal controller; and
a data-processing apparatus for data storage and processing, wherein said data-processing apparatus is associated with said laser source, said signal controller and said optical tuner setup module.

9. The system of claim 1 further comprising an AC/DC converter for rectification of said AC signal to said DC voltage output.

10. The system of claim 1 wherein said clamped component comprises an array of cantilevers with PZT films bound to a PCB.

11. The system of claim 10 wherein said clamped component further comprises a plurality of nickel mass sections, wherein each nickel mass section among said plurality of nickel mass sections is positioned on each of a cantilever array segment of a cantilever array, positioned thereon to accentuate an inertial momentum.

12. The system of claim 1 wherein said DC output voltage is accumulated across a capacitor.

13. The system of claim 1 wherein said clamped component comprises a plurality of DC output voltage terminals that are connected in parallel in order to achieve said electrical energy the form of said higher current output from said clamped component.

14. The system of claim 1 wherein said clamped component comprises a plurality of DC output voltage terminals that are connected in series in order to achieve said electrical energy in the form of said higher voltage output from said clamped component.

15. The system of claim 1 wherein said clamped component comprises a plurality of DC output voltage terminals that are connected in series-parallel in order to achieve said electrical energy in the form of said higher voltage and a higher current output from said clamped component.

16. An electrical energy harvesting system, comprising:
a waveform generator for generating a signal;
a vibrator for providing mechanical vibrations, wherein said vibrator is program-controlled by said waveform generator; and
an accelerator attached to said vibrator, wherein said accelerator measures a vibration strength of said mechanical vibrations and an amplitude or velocity of said signal, thereby permitting a clamped component subject to said accelerator and said vibrator to provide converted vibration energy in the form of an AC signal that is rectified to a DC voltage output in order to achieve an electrical energy in the form of a higher voltage or a current output that is harvested and utilized to characterize the electrical functioning of an associated electrical system or device; a power amplifier integrated with said waveform generator to drive said vibrator and regulate a vibration strength of said mechanical vibrations;
an accelerator monitor associated with said accelerator, wherein said accelerator monitor delivers a signal strength associated with said signal; and wherein a displacement laser sensor is attached to said clamped component for tip displacement testing.

17. A method for electrical energy harvesting, comprising:
providing a waveform generator that generates a signal;
associating a vibrator with said waveform generator, wherein said vibrator provides mechanical vibrations and wherein said vibrator is program-controlled by said waveform generator;
attaching an accelerator to said vibrator, wherein said accelerator measures a vibration strength of said mechanical vibrations and an amplitude or velocity of said signal; and
through a partnering dynamic, allowing a clamped component to provide converted vibration energy in the form of an AC signal, wherein said AC signal is utilized in a predominately non-diagnostic role and subsequently rectified to a DC voltage output in order to achieve an electrical energy in the form of a higher voltage or a higher current output that is harvested and utilized to characterize the electrical functioning of an associated electrical system or device, said clamped component comprising a plurality of nickel mass sections, wherein each nickel mass section among said plurality of nickel mass sections is positioned on each of a cantilever array segment of a cantilever array, positioned thereon to accentuate an inertial momentum.

18. The method of claim 17 further comprising integrating a power amplifier with said waveform generator to drive said vibrator and regulate a vibration strength of said mechanical vibrations; and associating an accelerator monitor with said accelerator, wherein said accelerator monitor delivers a signal strength associated with said signal.

19. The method of claim 17 further comprising providing a testing circuit comprising a bridge rectifier and a capacitor, wherein said testing circuit detects said electrical energy harvested and utilized to support the electrical functioning of an associated electrical system or device.

20. The method of claim 19 further comprising connecting an oscillograph to said testing circuit, wherein said oscillograph monitors a DC output voltage signal generated by said testing circuit.

21. The method of claim 17 further comprising providing a laser displacement sensor for tip displacement testing, wherein said laser displacement sensor is connected to said clamped component.

* * * * *